(12) United States Patent
Adzich et al.

(10) Patent No.: US 8,343,232 B2
(45) Date of Patent: Jan. 1, 2013

(54) FORTIFIED MESH FOR TISSUE REPAIR

(75) Inventors: Vaso Adzich, Santa Ana, CA (US); Stephen Graham Bell, Rome (IT); Giuseppe Amato, Palermo (IT)

(73) Assignee: Insightra Medical, Inc., Irvine, CA (US)

( * ) Notice: Subject to any disclaimer, the term of this patent is extended or adjusted under 35 U.S.C. 154(b) by 0 days.

(21) Appl. No.: 13/291,535

(22) Filed: Nov. 8, 2011

(65) Prior Publication Data

US 2012/0053602 A1    Mar. 1, 2012

Related U.S. Application Data

(62) Division of application No. 12/361,148, filed on Jan. 28, 2009.

(60) Provisional application No. 61/097,756, filed on Sep. 17, 2008, provisional application No. 61/024,489, filed on Jan. 29, 2008.

(51) Int. Cl.
*A61F 2/02* (2006.01)

(52) U.S. Cl. .................................................. 623/23.72

(58) Field of Classification Search .... 623/23.72–23.74, 623/23.76; 606/151, 213; 600/37
See application file for complete search history.

(56) References Cited

U.S. PATENT DOCUMENTS

| 6,551,356 B2 | 4/2003 | Rousseau |
| 2008/0147200 A1 | 6/2008 | Rousseau et al. |
| 2008/0262518 A1* | 10/2008 | Freudenthal .................. 606/151 |

OTHER PUBLICATIONS

Vaso Adzich, Stephen Graham Bell, Giuseppe Amato, "Fortified Mesh for Tissue Repair", pending U.S. Appl. No. 13/032,134 office action dated May 11, 2012.
Vaso Adzich, Stephen Graham Bell, Giuseppe Amato, "Fortified Mesh for Tissue Repair", pending U.S. Appl. No. 13/032,134 response filed May 25, 2012 to office action dated May 11, 2012.

* cited by examiner

*Primary Examiner* — Melanie Tyson
(74) *Attorney, Agent, or Firm* — John L. Rogitz

(57) ABSTRACT

A mesh to repair a hole in a muscle wall includes a resilient mesh body and fortifying structure such as mesh portions of thicker weave than other portions, or strengthening members that can be engaged with the mesh and then removed from the mesh once the mesh is place over the hole. The same principles can be applied to a plug that is engaged with the mesh for filling the hole.

22 Claims, 4 Drawing Sheets

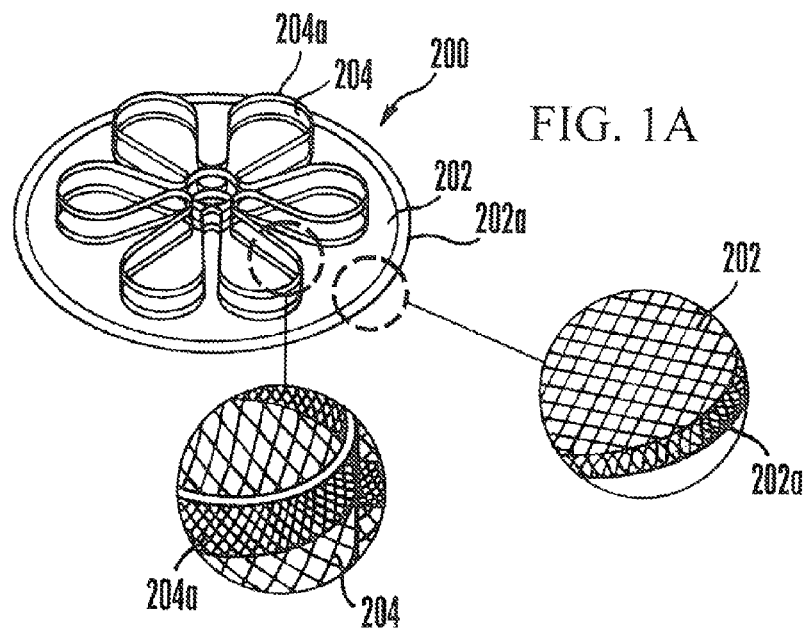
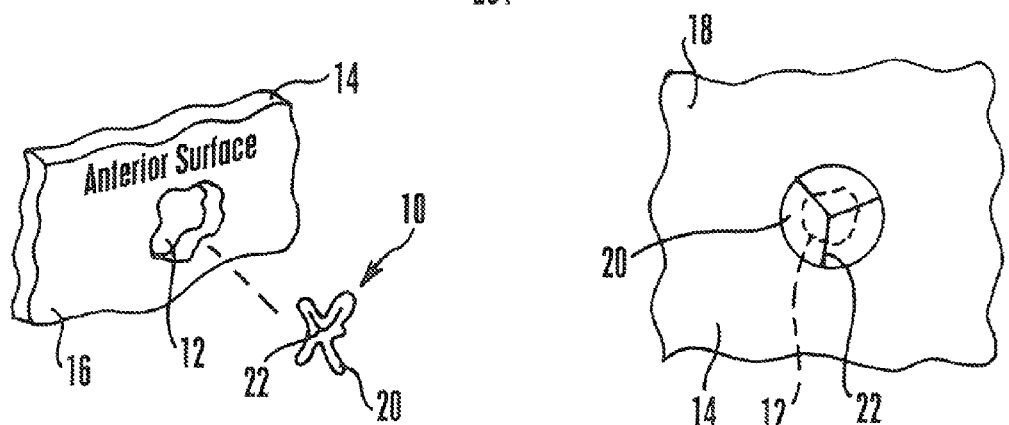
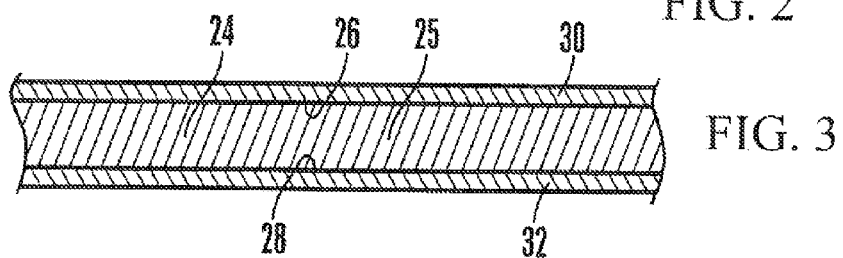
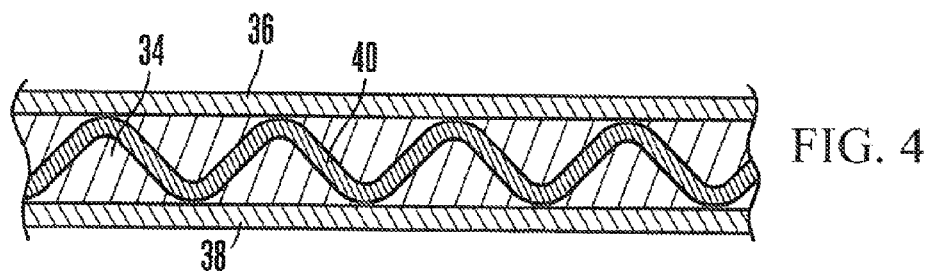

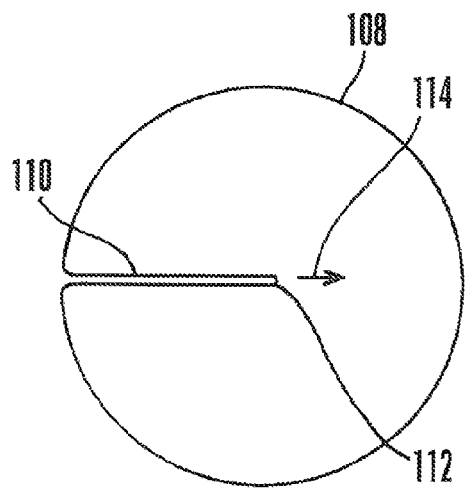
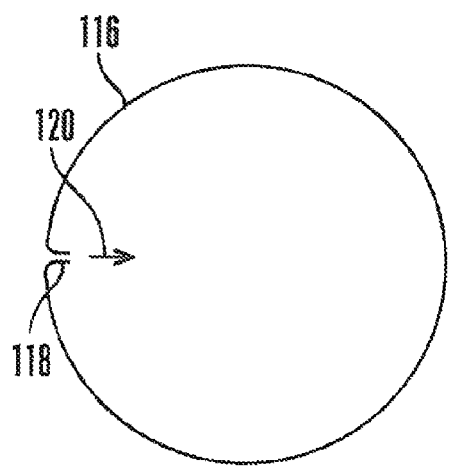
FIG. 15  FIG. 16
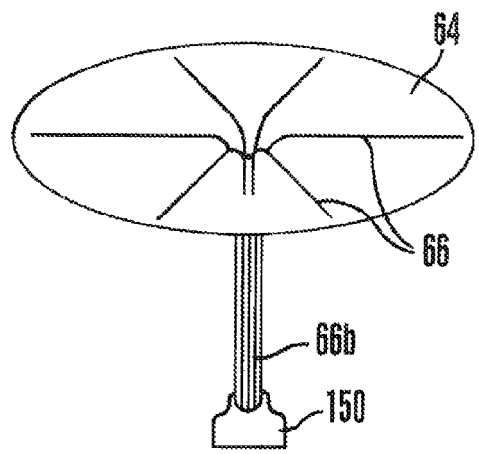
FIG. 17
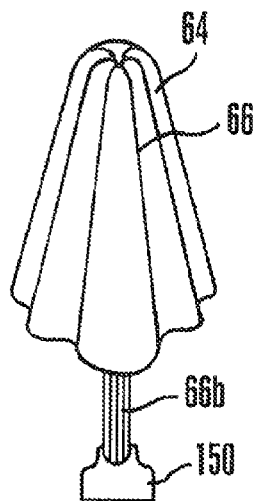
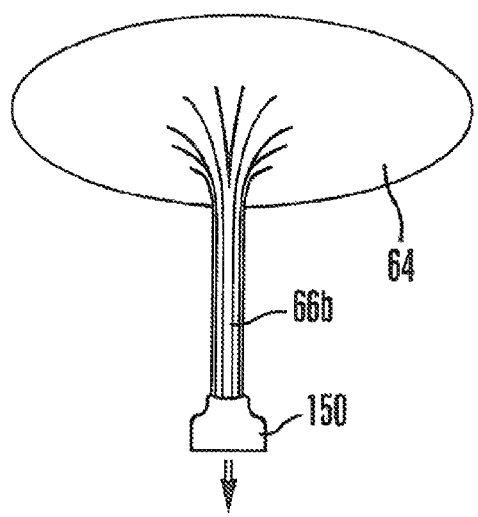
FIG. 18  FIG. 19

FORTIFIED MESH FOR TISSUE REPAIR

This application is a divisional of U.S. patent application Ser. No. 12/361,148, filed Jan. 28, 2009 which claims priority to U.S. provisional application 61/097,756, filed Sep. 17, 2008 which claims priority to U.S. provisional application 61/024,489, filed Jan. 29, 2008.

FIELD OF THE INVENTION

The present invention relates generally to the repair of defects in muscular structures, and more particularly to repairing hernias.

BACKGROUND OF THE INVENTION

A hernia is a condition in which part of the intestine bulges through a weak area in muscles of the abdomen. The main treatment for inguinal hernia is surgery to block the protrusion of abdominal content through the muscle wall. This surgery is called herniorrhaphy, and typically involves suturing the muscle layers and fascia together to reinforce the wall or blocking the defect with a flat polypropylene mesh.

As understood herein, the mesh must be sufficiently flexible and resilient to be pushed through a hole in a muscular wall for, e.g., hernia repair, pelvic floor prolapse, and other muscular repairs, and then assume a flat configuration against the posterior side of the wall as applicable.

SUMMARY OF THE INVENTION

As critically recognized herein, current meshes may not completely unfold into a flat configuration after being pushed through the muscle wall, and this condition is difficult to identify and/or remedy owing to poor visibility and/or access of the posterior side of the wall. As further recognized herein, increasing the resiliency of the mesh by increasing the filament diameter throughout the mesh can decrease the resiliency of the mesh and moreover increases the mass of the mesh to the point where tissue reaction with the mesh can increase undesirably.

Accordingly, an apparatus includes a flexible mesh having an insertion configuration, in which the mesh is smaller than a muscle hole to be repaired to facilitate advancing the mesh through the hole, and an implanted configuration, in which the mesh is substantially flat and larger than the hole to block the hole. A strengthening member is engaged with the mesh.

In some embodiments the strengthening member is removable from the mesh when the mesh is disposed against the hole in the implanted configuration. The strengthening member may be made of nitinol. The mesh can include a flexible mesh body and the strengthening member can include at least one filament engaged with the mesh body. Without limitation the filament may be a wire or a flat ribbon.

Plural filaments may be engaged with the mesh body. The filaments can be arranged on the mesh body in, e.g., a spoke configuration, a petal configuration, a spiral configuration, or a circular configuration. Filament ends may be exposed such that the ends can be grasped and the filaments pulled away from the mesh body.

In other embodiments the strengthening member can include strands of a thickness that is greater than the thickness of strands of the mesh body. The strengthening member may be made of one and only one (relatively thick) strand, or it may be made of plural strands and with a tighter weave than the weave of the strands of the mesh body.

In this latter embodiment the strengthening member can be disposed on at least one and preferably both of the surfaces of the mesh body. Or, it may be disposed around the periphery of the body. Yet again, it may be disposed on or between the surfaces and may be sinusoidal shape if desired. Plural strengthening members may be spaced from each other on the mesh body and may otherwise have different configurations from each other. The strengthening members may be concentric with each other or formed as a spiral.

In another aspect, a method includes providing a mesh body established by plural mesh strands. The mesh body is engaged with at least one strengthening member that is not a mesh strand. The method includes deforming the mesh body to a first configuration in which the mesh body can be advanced through a hole in a muscle wall. The method then includes advancing the mesh body through the hole and allowing the mesh body to assume a second configuration at least partially under influence of the strengthening member in which the mesh body expands to be larger than the hole and to be substantially flat. It is then ensured that the strengthening member does not subsequently fracture within the patient to contaminate or otherwise injure the patient.

In another aspect, a device to repair a hole in a muscle wall includes a resilient mesh body and fortifying structure. The fortifying structure may be mesh portions of greater thickness than portions of the mesh body, effectively forming ribs to provide greater strength to provide a leaf spring-like force without having to use a separate leaf spring, which might otherwise break away or fracture. Alternatively the fortifying structure may be strengthening members engaged with the mesh body and removable from the mesh body once the mesh is placed over the hole.

The details of the present invention, both as to its structure and operation, can best be understood in reference to the accompanying drawings, in which like reference numerals refer to like parts, and in which:

BRIEF DESCRIPTION OF THE DRAWINGS

FIG. 1A is a perspective view of an example mesh with integral plug portion woven into the mesh, with both the mesh and plug including strengthening members, showing two enlarged views to illustrate the strengthening members;

FIG. 1B is a perspective view of an example mesh in the insertion configuration about to be advanced through a hole in a muscle wall, with the plug portion removed for clarity;

FIG. 2 is an elevational view of the mesh in the implanted configuration positioned against the posterior surface of the wall blocking the hole, which is shown in phantom;

FIG. 3 is a side view of a first embodiment of the mesh or plug showing a strengthening member on the flat surfaces of the body;

FIG. 4 is a side view of another embodiment of the mesh (or plug) showing a strengthening members on the flat surfaces of the body as well as being disposed between the surfaces;

FIGS. 15 and 16 are plan views of a circular strengthening member showing free ends that can be grasped for removing the member; and FIGS. 17-19 are schematic views illustrating various operational aspects of example meshes.

DETAILED DESCRIPTION OF THE PREFERRED EMBODIMENT

Figure 5:
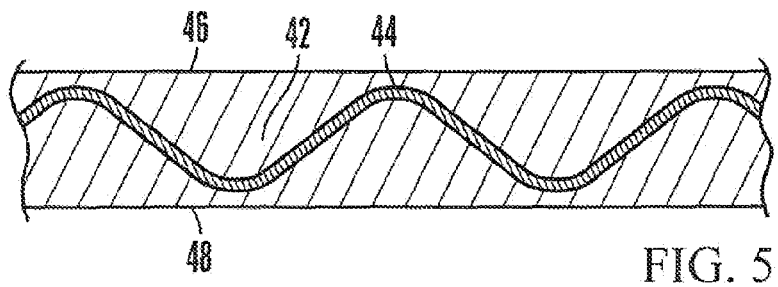
FIG. 5 is a side view of another embodiment of the mesh (or plug) showing a sinusoidal strengthening member disposed between the surfaces.

FIG. 1A shows a device 200 that includes a round deformable thread mesh 202 designed to lay against a muscle wall and a ribbon or thread plug 204 engaged with the mesh 202 and designed to fill a hole in the muscle wall. The plug 204 is formed of a ribbon of mesh strands in a flower petal configuration as shown. The plug 204 alternatively may be a plug disclosed in the present assignee's U.S. patent application Ser. No. 11/934,897, incorporated herein by reference.

The plug 204 and/or mesh 202 may be provided with strengthening members in accordance with disclosure below. Briefly, in the example shown strengthening members 202a are provided around the periphery of the mesh 202 while strengthening members 204a are provided around the peripheries of the tops and bottoms of each "petal" of the plug 204.

In the example shown, the strengthening members 202a, 204a are established by thread fibers that are more closely knitted together than the fibers of the mesh 202/plug 204. The fibers of the strengthening members 202a, 204a, which individually may be the same size or smaller (e.g., a mil in diameter smaller) than the fibers of the mesh 202 and plug 204, are woven (including as by knitting or sewing) into the fibers of the mesh 202 and plug 204, respectively. This creates additional stiffness by concentrating more material in one area, resulting in increased fiber density, increased thickness, or both.

In example non-limiting embodiments the mesh 202 can be knitted in an open weave pattern, using polypropylene fibers three to eight mils in diameter. The mesh 202 can have a pore size of between eight-tenths of a square millimeter and sixteen square millimeters (0.8 mm$^2$-16 mm$^2$). To establish the strengthening member 202a, polypropylene fibers of, e.g., three to eight mils in diameter are sewn around the edge of the mesh 202 in a close knit sewing pattern and/or multiple passes can be made around the edge to build up additional fiber density. For example, the fiber density of the strengthening member 202a may be ten to one hundred times the fiber density of the remainder of the mesh 202.

As an alternate means of construction stiffer regions with additional fibers, additional fiber material can be welded to the mesh material. Similarly to when the additional fibers are woven into the material, the additional fibers are integrated to the mesh material and cannot be easily removed.

For instance, a polypropylene mesh ring can be constructed of fibers three to eight mils in diameter. One to four additional rings, each one-tenth of an inch to a half an inch in width, of the same material and of the same outer diameter as the mesh 202 can then be welded onto the mesh 202. This creates additional fiber density (as viewed from the top) on the edge of the mesh 202, creating a stiffer material in selected locations, biasing the material in a wrinkle free condition.

Likewise, present principles set forth above contemplate that the plug 204 can have both stiffness and elasticity, so that the combination of structure has a resistance to crush, but can still return to an original configuration if deformed. In some embodiments the overall amount of material may be minimized, and the stiffness can be anisotropic. This may be achieved by increasing the fiber density in specific regions in the same manner as described above.

In greater detail, a knitted mesh material can be knitted into a strip with a more open knit in the middle (pore size of between eight-tenths of a square millimeter and sixteen square millimeters (0.8 mm$^2$-16 mm$^2$) and significantly greater fiber density (length of fiber in a given area) at the edges (fiber density ten to one hundred times greater than in the base material) using a polypropylene fiber three to eight mils in thickness. This strip can then be heat set into a final weave configuration and further heat set into a petal configuration. This particular method creates resistance to circumferential crush on the sides of the petals, but minimal resistance to crush from the top.

As the fiber thickness increases, the stiffness increases, but the elasticity (i.e. the ability to return to a given shape after being deformed) decreases. Therefore, the amount of fibers and fiber thickness can be established to obtain the desired combination of stiffness and elasticity. Specifically, in example non-limiting embodiments the mesh 202/plug 204 can be knitted of a polypropylene fiber of between four to eight mils in diameter while the fibers that establish the strengthening members 202a, 204a can be one-half mil to three mils smaller in diameter than those used in the mesh 202/plug 204, and can be knitted to the edges of the mesh 202/plug 204 in a denser configuration to produce specific material properties. To increase the resistance to crush from the top, additional fibers may be knitted in a sinusoidal pattern into the middle of the plug 204.

Referring now to FIGS. 1B and 2, a device is shown, generally designated 10, for blocking an opening 12 of a muscle wall 14 that may have an anterior surface 16 and a posterior surface 18. As shown, the device 10 includes a mesh body 20 and one or more stiffening members 22 for fortifying the body 20. The device 10 may be established by any of the specific embodiments described below. Without limitation the mesh can be made of polypropylene, expanded polytetrafluoroethylene (PTFE), polyester, biodegradable materials, the material marketed as "dualmesh", a trademark of W. L. Gore, or even metal such as stainless steel or nitinol, or some combination thereof. It is to be understood that the device 10 may include the plug 204 described above, with the plug being omitted in this and subsequent views of mesh embodiments for clarity only.

The device 10 can be moved between an insertion configuration (FIG. 1), in which the device 10 is smaller than the hole 12 to facilitate advancing the device 10 through the hole 12, and an implanted configuration (FIG. 2), in which the device 10 is substantially flat and unwrinkled/unfolded and is larger than the hole 12 to block the hole 12. As will be clearer after disclosure below, the device 10 is biased to the implanted configuration at least by the strengthening member 22 and in some implementations by the mesh body 20 as well. Thus, the device 10 is resilient and is materially biased to the implanted configuration.

The wall 14 may be, as an example, a wall of an abdomen muscle in which the hole 12 has formed as a hernia. Typically, the device 10 may be deformed to the insertion configuration, advanced through the hole 12 from the anterior surface 16 until it clears the hole 12, and then permitted (as by releasing the device 10) to assume the implanted configuration in which the device 10 lies flat against the posterior surface 18 of the wall 14, blocking the hole 12. Defects in other muscle walls may be similarly resolved using the device 10. Other muscle wall defects such as pelvic floor prolapse may be similarly resolved.

FIG. 3 shows a first embodiment of the device 10 that includes a mesh body 24 composed of a matrix of strands 25 that are relatively thin in diameter and that may be knitted or woven together usually although not exclusively in a symmetric mesh pattern. It is to be understood that the structure of FIGS. 3-6 may also be used to establish the above-described plug 204 with strengthening members 204a.

Without limitation the strands 25 may be a polymer such as but not limited to polypropylene or a biodegradable material. The strands 25 may alternatively be metal such as nitinol or stainless steel or a combination of metal and polymer. The strands 25 typically have the same diameter as each other but may have differing diameters.

In the example embodiment shown in FIG. 3, the mesh body 24 defines opposed surfaces 26, 28 that are flat in the implanted configuration shown. A first strengthening member 30 may be engaged along the edge of the surface 26 of the mesh body 24 as shown. In some embodiments a second strengthening member 32 may be engaged with the edge of the other surface 28.

As contemplated by the embodiment of FIG. 3, each strengthening member includes one or more segments that are thicker than the strands 25 of the mesh body 24, either by virtue of being individually thicker strands or by virtue, as described above, of being a combination of more tightly woven strands. Thus, in one implementation each segment of the strengthening member is a single relatively thick strand; in other implementations each segment of the strengthening member may be plural relatively thin strands that are woven together in a tighter weave than are the strands 25 of the mesh body 24 to form a single composite strand, although the strands of a multi-strand segment may be larger than the strands of the unfortified portions of the mesh. In any case, the strengthening members 30, 32 may be engaged with the mesh body 24 by weaving the strands of the strengthening members into strands 25 of the mesh body 24. The effect is to increase the stiffness and elasticity/resiliency of the resulting mesh compared to what it would be without the strengthening members.

FIG. 4 shows that a mesh body 34 may be engaged with surface strengthening members 36, 38 that are in all essential respects identical in configuration and function to the members 30, 32 shown in FIG. 3, and in addition a third strengthening member 40 may be provided between the surfaces of the mesh body 34 as shown. The third member 40 may be non-linear and in the embodiment shown may be sinusoidal. Or, as shown in FIG. 5 a mesh body 42 may be engaged with only a single internal strengthening member 44 disposed between surfaces 46, 48 of the mesh body 42, omitting strengthening members on the outer surfaces of the mesh body.

Figure 6:
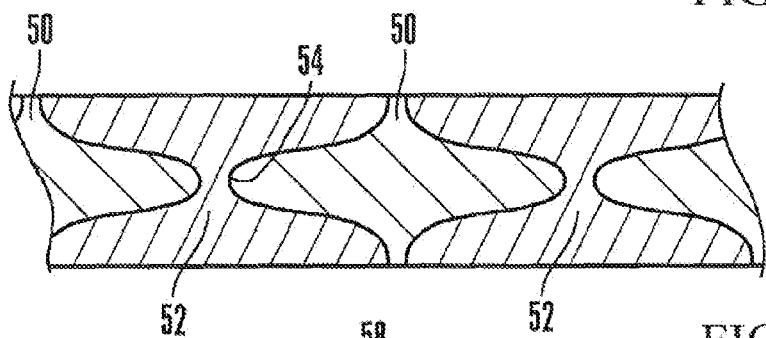
FIG. 6 is a side view of another embodiment of the mesh (or plug) showing strengthening members spaced from each other on the body.

FIG. 6 shows that a mesh body 50 may be engaged with plural internal strengthening members 52 that are spaced from each other on the mesh body 50. The members 52 in FIG. 6 are generally hourglass-shaped with each having a respective relatively narrow waist 54 as shown, although other shapes may be used. The strengthening members 52 furthermore may each be of a different configuration than other strengthening members, e.g., of a different shape, size, width, height, and weave pattern.

Figure 7:
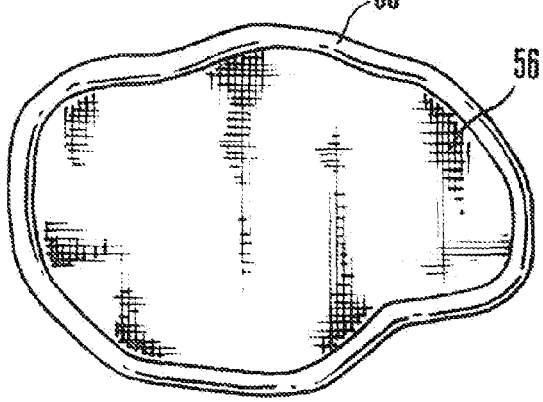
FIG. 7 is a plan view of another embodiment of the mesh showing strengthening members disposed on the periphery of the body.

FIG. 7 shows a mesh body 56 that defines a periphery, and a strengthening member 58 is disposed on the periphery as shown by, e.g., weaving the strengthening member into the periphery. The periphery may be circular, ovular, polygonal, or other closed form.

Figure 8:
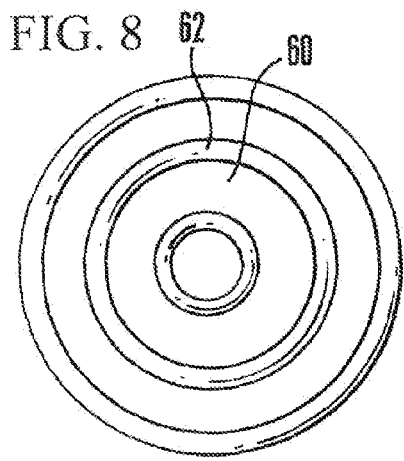
FIG. 8 is a plan view of another embodiment of the mesh showing plural concentric strengthening members on the body.

As yet another alternative, FIG. 8 shows a mesh body 60 that is engaged with plural concentric strengthening members 62. One of the members 62 may be woven into the periphery of the mesh body and internal, smaller members 62 may be woven into the interior of the mesh body as shown. While the members 62 are shown as forming closed circles, they need not be complete circles in some embodiments.

The structures shown in FIGS. 3-8 may be made in a single knitting/weaving process to establish the mesh body and the strengthening members. Alternatively the mesh body may be knitted/woven and the strengthening members may be knitted or woven separately, and then a second step of weaving/knitting can be used to weave the strengthening members into the mesh body to incorporate the strengthening members into the mesh body. Heat engagement such as by welding/melting may alternatively be used. Additional material processing such as heat treating/annealing may be used in accordance with principles known in the art.

Figure 9:
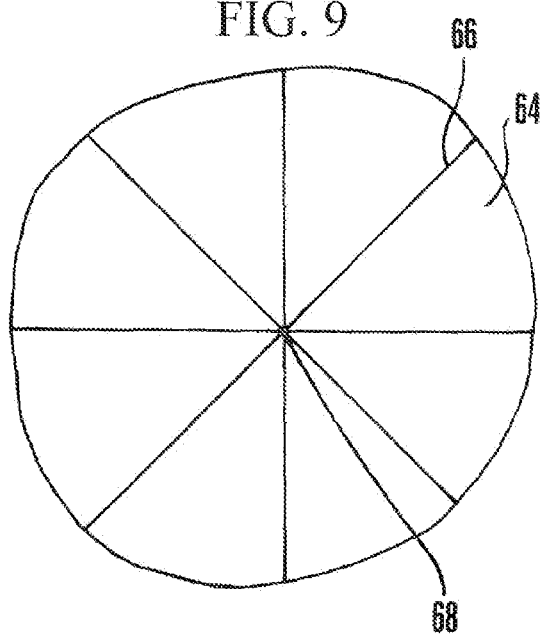
FIG. 9 is a plan view of removable filament-like strengthening members arranged on the mesh body in a spoke configuration, with the top surface of the mesh body removed to show the strengthening members.
Figure 10:
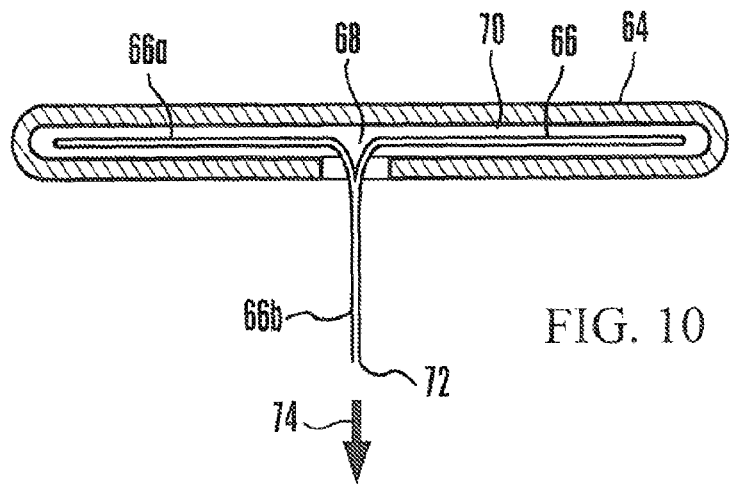
FIG. 10 is a side view of the strengthening members shown in FIG. 9.

While FIGS. 3-8 illustrate strand-based strengthening members that are interwoven with the mesh body to strengthen the mesh while reducing the risk of a strengthening member breaking off into the patient's body, FIGS. 9-19 illustrate flexible filament-like strengthening members (configured as round wires or flat ribbons or other cross-sectional shape) that are removed from the mesh body after implantation (when the mesh is disposed against the hole in the implanted configuration) to reduce the same risk. In FIGS. 9 and 10, a mesh body 64 that in all substantial respects may be identical to the mesh bodies described previously is engaged with plural spoke-like strengthening members 66 that extend from the middle 68 of the mesh body 64 along respective radials. Without limitation, the members 66 may be made of a shape memory material such as nitinol, or they may be made of other metal or polymer; the same comment applies to the strengthening members described in the ensuing figures.

As shown best in FIG. 10, each member 66 may be disposed in a respective channel 70 of the mesh body 64, it being understood that the mesh body 64 may be composed of two disk-shaped layers between which the channels 70 are formed. The members 66 alternatively may be disposed in respective seams or grooves. In the embodiment shown in FIG. 10, each member 66 includes a radial member 66a extending in the mesh body 64 along a radial dimension defined by the mesh body, and an axial segment 66b extending axially down from a hole formed in the middle 68 of the mesh body. The ends 72 of the axial segments 66b may be grasped and pulled as shown by the arrow 74 to remove the members 66 from the mesh body 64 after implantation of the mesh body over the muscle hole and assumption of the mesh body 64 of the implantation configuration, in which the mesh body substantially is flat and is not folded or wrinkled.

Figure 11:
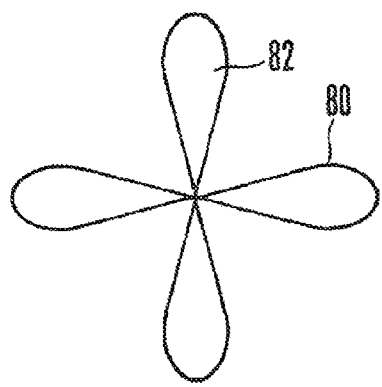
FIGS. 11-13 are views of removable filament-like strengthening members arranged in various petal configurations for placement in or on a mesh.
Figure 12:
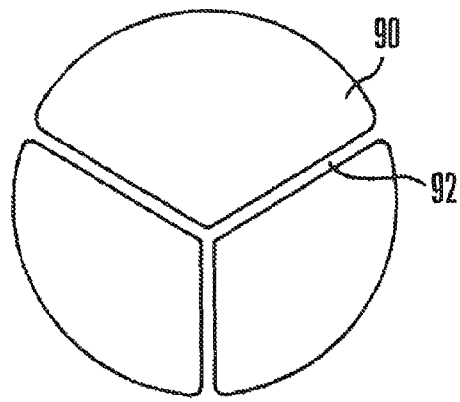
Figure 13:
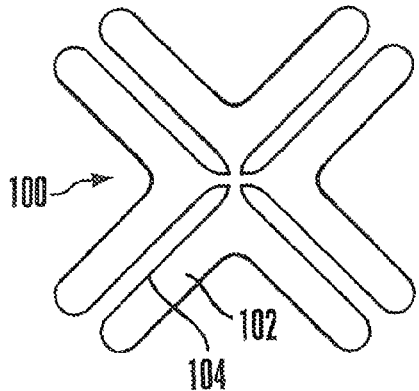

FIGS. 11-13 respectively show alternative strengthening members 80, 90, 100 that are petal-shaped. In FIG. 11, a strengthening member 80 is configured as orthogonal "figure 8"s having four lobes 82 staggered azimuthally by 90°. In FIG. 12, three strengthening members 90 are provided as thirds of a pie-like structure, with adjacent members 90 being separated by narrow channels 92. In FIG. 13, a strengthening member 100 has four V-shaped lobes 102 staggered by 90° such that the long side 104 of one "V" is parallel to and closely spaced from a long side of an adjoining "V" as shown.

Figure 14:
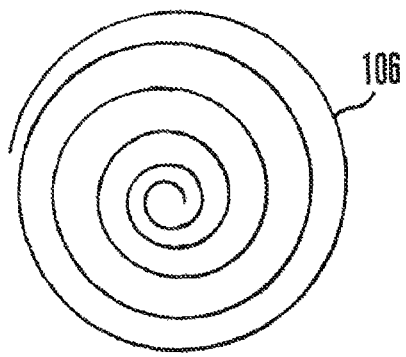
FIG. 14 is a plan view of removable filament-like strengthening members arranged on the mesh body in a spiral configuration.

As another alternative, in FIG. 14 a spiral-shaped strengthening member 106 may be engaged with a mesh body of the present invention. In another alternative, a circular strengthening member 108 in FIG. 15 may include two straight co-parallel segments 110 extending radially inwardly on the mesh body and having respective ends 112 that may be grasped at the center of the member 108 for removing the member 108 from the mesh body, as indicated by the arrow 114. Or, a circular strengthening member 116 in FIG. 16 may include two short segments 118 extending radially that may be grasped at or near the periphery of the member 116 for removing the member 116 from the mesh body, as indicated by the arrow 120.

FIGS. 17-19 illustrate operational aspects of the filament-type devices using as an example the device shown and described in reference to FIGS. 9 and 10. The mesh body 64 may be deformed into the insertion configuration shown in FIG. 18, in which the mesh body 64 is folded into an umbrella-like shape. The body can be collapsed by pushing it against, into, and through the hole sought to be covered.

Once positioned as desired over the surface of the wall having a hole sought to be covered, the mesh body 64 is released, e.g., by clearing the hole, to assume the implanted configuration shown in FIG. 17, with the axial segments 66b extending back through the hole in one embodiment. A removal member 150 may then be used to grasp the ends of the axial segments 66b as shown and pulled as indicated in FIG. 19 to pull the strengthening members 66 out of the implanted mesh body 64 to ensure that the strengthening members do not subsequently fracture within the patient to contaminate or puncture the patient. In some embodiments the strengthening members 66 may not be installed in the mesh until the mesh is in place on the posterior side of the wall, at which point they may be installed to reform the mesh into the flat configuration and then removed.

The strengthening members may be removed simultaneously with each other as shown or one at a time. Removal can be effected by pulling at one end as shown or by pulling from multiple locations.

While the particular FORTIFIED MESH FOR TISSUE REPAIR is herein shown and described in detail, it is to be understood that the subject matter which is encompassed by the present invention is limited only by the claims.

What is claimed is:

1. Apparatus, comprising:
a flexible mesh having an insertion configuration, in which the mesh is radially smaller than a muscle hole to be repaired to facilitate advancing the mesh through the hole, and an implanted configuration, in which the mesh is substantially flat and larger than the hole to block the hole;
a plug engaged with a surface of the mesh and having a closed top periphery defining plural lobe-shaped petals configured to fill the muscle hole to be repaired;
a first strengthening member provided on the closed top periphery of the plug;
the plug defining a closed bottom periphery defining plural lobe-shaped petals, a second strengthening member being provided around the closed bottom periphery.

2. The apparatus of claim 1, comprising a mesh strengthening member provided on a periphery of the mesh.

3. The apparatus of claim 2, wherein the mesh strengthening member is made of polypropylene fibers of three to eight mils in diameter that are sewn around the periphery of the mesh in a close knit sewing pattern.

4. The apparatus of claim 2, wherein the mesh strengthening member includes fibers defining a fiber density and the mesh includes fibers defining a fiber density and a fiber density of the mesh strengthening member is ten to one hundred times a fiber density of the mesh.

5. The apparatus of claim 1, wherein the mesh includes fibers and the first strengthening member is established by fibers that are more closely woven together than fibers of the mesh.

6. The apparatus of claim 1, wherein the plug includes fibers woven together and the first strengthening member is established by fibers that are more closely woven together than fibers of the plug.

7. The apparatus of claim 1, wherein the plug includes fibers and the first strengthening member includes fibers and fibers of the first strengthening member individually are no larger than fibers of the plug.

8. The apparatus of claim 1, wherein the mesh includes fibers and the first strengthening member includes fibers and fibers of the first strengthening member individually are no larger than fibers of the mesh.

9. The apparatus of claim 1, wherein the plug includes fibers and the first strengthening member includes fibers and fibers of the first strengthening member are woven into fibers of the plug.

10. The apparatus of claim 1, wherein the mesh is woven in an open weave pattern.

11. The apparatus of claim 10, wherein the mesh is made of polypropylene fibers three to eight mils in diameter.

12. The apparatus of claim 11, wherein the mesh has a pore size of between eight-tenths of a square millimeter and sixteen square millimeters (0.8 mm$^2$-16 mm$^2$).

13. A device to repair a hole in a muscle wall, comprising:
a resilient fiber body including first and second fiber portions; and
fortifying structure established by the first fiber portions of the fiber body, the first fiber portions of the fiber body being of greater thickness than the second fiber portions of the fiber body and being interwoven with the second fiber portions of the fiber body to define a flower petal-shaped structure, wherein the second fiber portions of the fiber body is a plug having a closed periphery defining plural lobe-shaped petals configured to fill the hole in the muscle wall to be repaired, the fortifying structure being disposed on the closed periphery of the plug wherein the closed periphery is a top periphery, the fortifying structure is a first fortifying structure, and the plug defines a closed bottom periphery defining plural lobe-shaped petals, a second fortifying structure being provided around the closed bottom periphery.

14. The device of claim 13, comprising a mesh fortifying structure provided on a periphery of a mesh, the mesh being coupled to the plug.

15. The device of claim 14, wherein the mesh includes fibers and the mesh fortifying structure is established by fibers that are more closely woven together than fibers of the mesh.

16. The device of claim 14, wherein the mesh fortifying structure is made of polypropylene fibers of three to eight mils in diameter that are sewn around the periphery of the mesh in a close knit sewing pattern.

17. The device of claim 14, wherein the mesh has fibers defining a fiber density and the mesh fortifying structure has fibers defining a density and a fiber density of the mesh fortifying structure is ten to one hundred times a fiber density of the mesh.

18. The device of claim 13, wherein the plug includes fibers woven together and the fortifying structure is established by fibers that are more closely woven together than fibers of the plug.

19. The device of claim 13, wherein fibers of the fortifying structure individually are no larger than fibers of the second fiber portions of the fiber body.

20. The device of claim 13, wherein the second fiber portions of the fiber body are woven in an open weave pattern.

21. The device of claim 20, wherein the second fiber portions of the fiber body are made of polypropylene fibers three to eight mils in diameter.

22. The device of claim 21, wherein the second fiber portions of the fiber body have a pore size of between eight-tenths of a square millimeter and sixteen square millimeters (0.8 mm$^2$-16 mm$^2$).

* * * * *